(12) United States Patent
Srnka et al.

(10) Patent No.: US 8,436,609 B2
(45) Date of Patent: May 7, 2013

(54) METHOD AND APPARATUS FOR DETECTION OF A LIQUID UNDER A SURFACE

(75) Inventors: Leonard J. Srnka, Bellaire, TX (US);
Timothy J. Nedwed, Houston, TX (US);
Hans Thomann, Bedminister, NJ (US);
Robert E. Sandstrom, Sugar Land, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 325 days.

(21) Appl. No.: 12/672,969

(22) PCT Filed: Aug. 29, 2008

(86) PCT No.: PCT/US2008/074874
§ 371 (c)(1),
(2), (4) Date: Feb. 10, 2010

(87) PCT Pub. No.: WO2009/045670
PCT Pub. Date: Apr. 9, 2009

(65) Prior Publication Data
US 2011/0181279 A1      Jul. 28, 2011

Related U.S. Application Data

(60) Provisional application No. 60/997,876, filed on Oct. 5, 2007.

(51) Int. Cl.
*G01V 3/00* (2006.01)
(52) U.S. Cl.
USPC .............................. 324/303; 324/306; 324/318
(58) Field of Classification Search .......... 324/300–322; 600/407–435; 382/128–131
See application file for complete search history.

(56) References Cited

U.S. PATENT DOCUMENTS

| 3,019,383 A | 1/1962 | Varian |
| 3,665,466 A | 5/1972 | Hibbard |

(Continued)

FOREIGN PATENT DOCUMENTS

WO    WO 2009/013503 A1    1/2009

OTHER PUBLICATIONS

Dickens, D. et al., "Detection and Tracking of Oil under Ice", US Department of the Interior, Minerals Management Service, Oct. 6, 2000, pp. 1-53.

(Continued)

*Primary Examiner* — Melissa Koval
*Assistant Examiner* — Tiffany Fetzner
(74) *Attorney, Agent, or Firm* — ExxonMobil Upstream Research Company Law Dept.

(57) ABSTRACT

Methods for detecting a liquid under a surface and characterizing Ice are provided The liquid may be a liquid hydrocarbon such as crude oil or fuel oil or mineral oil The surface may be ice, snow, or water, and the method may be practiced in an arctic region to detect oil spills, leaks, or seepages The methods may be used with a range finder to characterize marine ice The methods may include a nuclear magnetic resonance (NMR) tool with antenna to send a radio-frequency (RF) excitation pulse or signal into volume of substances being detected, detect an NMR response signal to determine the presence of the liquid of interest The NMR response may include a relaxation time element and an intensity level and may include a free induction signal (T2*), a spin echo signal (T2), a train of spin echo signals (T2), or a thermal equilibrium signal (T 1).

18 Claims, 6 Drawing Sheets

U.S. PATENT DOCUMENTS

| | | | |
|---|---|---|---|
| 4,022,276 | A | 5/1977 | Dreher et al. |
| 4,053,406 | A | 10/1977 | Deslauriers et al. |
| 4,449,047 | A | 5/1984 | Monroe |
| 4,595,878 | A * | 6/1986 | Bradshaw ............... 324/300 |
| 4,769,602 | A | 9/1988 | Vinegar et al. |
| 4,868,500 | A | 9/1989 | Baldwin et al. |
| 5,433,717 | A * | 7/1995 | Rubinsky et al. ............ 606/20 |
| 5,517,115 | A | 5/1996 | Prammer .................. 324/303 |
| 5,583,437 | A * | 12/1996 | Smith et al. ............... 324/307 |
| 5,602,477 | A * | 2/1997 | McCarthy et al. ........... 324/315 |
| 5,673,050 | A | 9/1997 | Moussally et al. ............ 342/22 |
| 5,706,810 | A * | 1/1998 | Rubinsky et al. ........... 600/412 |
| 5,903,153 | A | 5/1999 | Clarke et al. |
| 5,999,836 | A | 12/1999 | Nelson et al. ............... 600/407 |
| 6,177,794 | B1 | 1/2001 | Stoeffl |
| 6,177,797 | B1 * | 1/2001 | Srinivasan ................. 324/318 |
| 6,216,540 | B1 | 4/2001 | Nelson et al. ................. 73/633 |
| 6,345,194 | B1 | 2/2002 | Nelson ....................... 600/425 |
| 6,346,813 | B1 | 2/2002 | Klenberg .................... 324/303 |
| 6,621,448 | B1 | 9/2003 | Lasky et al. ................... 342/22 |
| 6,690,316 | B2 | 2/2004 | Yankielun ...................... 342/22 |
| 6,794,864 | B2 | 9/2004 | Mirotchnik et al. |
| 6,825,657 | B2 | 11/2004 | Kleinberg et al. ............ 324/303 |
| 6,867,589 | B2 | 3/2005 | Heaton |
| 6,891,369 | B2 | 5/2005 | Hurlimann et al. |
| 7,253,617 | B1 | 8/2007 | Chen et al. |
| 7,298,142 | B2 | 11/2007 | Hursan et al. |
| 7,423,426 | B2 | 9/2008 | Reiderman .................. 324/303 |
| 7,663,363 | B2 | 2/2010 | Reiderman .................. 324/303 |
| 8,294,468 | B2 | 10/2012 | Reiderman .................. 324/346 |
| 2003/0020647 | A1 | 1/2003 | Yankielun |
| 2005/0189945 | A1 | 9/2005 | Reiderman .................. 324/333 |
| 2006/0255799 | A1 | 11/2006 | Reiderman |
| 2007/0047117 | A1 | 3/2007 | Wang |
| 2008/0206887 | A1 | 8/2008 | Chen et al. |
| 2008/0284426 | A1 | 11/2008 | Shorey et al. |
| 2011/0181279 | A1 * | 7/2011 | Srnka et al. .................. 324/307 |
| 2012/0165215 | A1 * | 6/2012 | Andersen et al. ................ 506/9 |

OTHER PUBLICATIONS

Dickens, D. F., "2006 Svalbard Experimental Spill to Study Spill Detection and Oil Behavior in Ice", US Department of the Interior, Minerals Management Service, Dec. 15, 2006, pp. 1-52.

Gev, I. et al., "Detection of the water level in fractured phreatic aquifers using nuclear magnetic resonance (NMR) geophysical measurements", Journal of Applied Geophysics, Jan. 3, 1990, pp. 277-282, v. 34, Elsevier, UK.

Legchenko, A. et al., "Nuclear magnetic resonance as a geophysical tool for hydrogeologists", Journal of Applied Geophysics, 2002, pp. 21-46, v. 50, Elsevier, UK.

Mohnke, O. et al., "Smooth and block inversion of surface NMR amplitudes and decay times using simulated annealing", 2002, pp. 163-177, v. 50, Elsevier, UK.

Pape, H. et al., "Pore geometry of sandstone derived from pulsed field gradient NMR", Journal of Applied Geophysics, 2006, pp. 232-252, v. 58, Elsevier, UK.

Ramasami, V. et al., "A low frequency wideband depth sounder for sea ice", 2003, IEEE, 3 pages.

Shushakov, O. A. et al., "Hydrocarbon Contamination of Aquifers by SNMR Detection", WM Conference, Feb. 29-Mar. 4, 2004, 7 pages, Tucson, AZ.

Weichman, P. B. et al., "Study of surface nuclear magnetic resonance inverse problems", Journal of Applied Geophysics, 2002, pp. 129-147, v. 50, Elsevier, UK.

* cited by examiner

METHOD AND APPARATUS FOR DETECTION OF A LIQUID UNDER A SURFACE

CROSS REFERENCE TO RELATED APPLICATIONS

This application is the National Stage of International Application No. PCT/US2008/074874, filed Aug. 29, 2008, which claims the benefit of U.S. Provisional Application No. 60/997,876, filed Oct. 5, 2007.

BACKGROUND

This application generally relates to a method and apparatus for the detection of a liquid under a surface. More particularly, a method of remotely detecting oil spilled under a layer of ice, snow, or water is disclosed herein.

This section is intended to introduce various aspects of the art, which may be associated with exemplary embodiments of the present invention. This discussion is believed to assist in providing a framework to facilitate a better understanding of particular aspects of the present invention. Accordingly, it should be understood that this section should be read in this light, and not necessarily as admissions of prior art.

Oil production or transfer in ice-prone marine or freshwater locations could result in a subsurface release—for example from a well blowout or leaking pipeline—that results in oil trapped beneath ice. Oil-spill countermeasures will require that this oil is accurately located and mapped. Currently, there is no effective technique to remotely sense the location and extent of a spill under ice. Characterizing ice (e.g. thickness, age, and extent) in these areas is also important for conducting hydrocarbon recovery and response operations, and determining potential impact loads on offshore structures.

The detection of oil under ice has been of concern since the exploration and production for hydrocarbon resources in the Arctic began in the early 1970's. There have been numerous attempts to detect oil under ice using acoustics, optical/UV excitation, and ground penetrating radar (for a review, see "Detection and Tracking of Oil under Ice", D. F. Dickins, report submitted to the US Department of the Interior Minerals Management Service, Oct. 6, 2000). All of these techniques have shown the capability to detect oil under ice with some success; however, they have not been used in the field. The methods proposed to date have a limited range of applicability and are susceptible to false positive results. They also have only a limited ability to "see" or detect oil through a layer of ice and require contact with the ice surface.

Notably, all three methods require access and traverse across the ice surface, some require the removal of snow cover, and special care must be taken to ensure good ice contact with the sensor. The surface access limitation presents both logistic and safety concerns such as breakthrough, and limits the coverage to a small area per day.

Dickins, et al. (2006) successfully detected oil under ice using ground-penetrating radar using a skid-mounted unit pulled along the ice surface (see "2006 Experimental Spill to Study Spill Detection and Oil Behavior in Ice", D. F. Dickins, P. J. Brandvik, L. G. Faksness, J. Bradfor, and L. Liberty; report submitted to the US Department of the Interior Minerals Management Service, Dec. 15, 2006, contract number 1435-0106-CT-3925). Tests with the system mounted in a helicopter were less conclusive although additional research is planned.

Up to this point, the only remote-detection technique to provide a direct signal from oil is the optical/UV detection method. However, this technique is limited to the detection of oil at the surface or only a few millimeters below the surface because the opaque nature and heterogeneity of both ice and snow scatter the luminescence to obscure the signal. Current techniques for detecting oil under ice are not effective or accurate enough to support a proper response in the event of an oil spill. In addition, these techniques are labor-intensive and dangerous due the surface contact requirement.

Ice characterization technology is similarly limited to ground penetrating radar (GPR), electromagnetic (EM), and satellite detection methods. GPR provides reliable thickness measurements for low salinity ice, but significant signal attenuation occurs for high-salinity first-year ice. EM methods measure ice plus snow thickness and require in-situ measurements. Satellite measurements in the infrared band only work for thin ice because surface temperature becomes less dependent on thickness for ice greater than 1.2 meters thick.

Nuclear magnetic resonance ("NMR") is a tool used for the characterization of the molecular composition of liquids and solids. More particularly, in some applications NMR is used to distinguish between a solid (e.g. rock in the earth) and a liquid (e.g. ground water or oil). NMR molecular characterization works by placing a sample in a magnetic field to align the magnetic moments of the protons with the field. The proton magnetic moments are then perturbed using one or more radio-frequency (RF) excitation pulses. The energy released as these magnetic moments return to equilibrium is monitored by a receiver.

In the oil and gas industry, NMR is applied in reservoir characterization in the field for well logging measurements and in laboratory analysis of rock cores. The NMR logging tool technology is capable of directly detecting the signals from fluids in the rock pore space and differentiating between different types and phases of fluids. In well logging, a magnet and a radio-frequency generator/receiver is lowered into the bore hole. NMR well logging tools, such as those in commercial use by oilfield service companies such as Schlumberger, Halliburton and BakerHughes, detect fluids in the pore space over a volume on the order of several cubic decimeters ($dm^3$). An example of such a tool is NUMAR™ by Schlumberger.

NMR has also been used to detect aquifers (e.g. an underground formation including ground water). Such instruments typically utilize the earth's magnetic field as the static magnetic field, detect a larger volume than the downhole devices (cubic meters ($m^3$) rather than $dm^3$), and are placed on the earth's surface for operation. Examples of such a system are NUMIS™ and NUMIS PLUS™ by Heritage Geophysics. These devices typically utilize a 100 meter diameter wire loop placed flat on the ground as the sending/receiving antenna. The large loop permits the sensing of aquifers over a larger volume than the downhole devices ($m^3$ v. $dm^3$) and greater depths (up to 150 m). A measurement time of about one hour per detection volume is typically required. Current NMR research in geophysical applications addresses difficulties that arise when attempting to identify liquids located in pores or at a surface between a liquid and a solid. See, e.g., PAPE, et al., Pore Geometry of Sandstone Derived from Pulsed Field Gradient NMR, J. of Applied Geophysics 58, pp. 232-252 (2006).

While NMR tools have been used for a variety of applications, the technology has not been used to detect oil spilled under a surface such as water, ice, or snow, nor has it been used to characterize ice.

Other useful information may be found in the following references: U.S. Pat. No. 3,019,383; U.S. Pat. No. 4,022,276;

U.S. Pat. No. 4,769,602; U.S. Pat. No. 4,868,500; Gev, et al., Detection of the Water Level of Fractured Phreatic Aquifers Using Nuclear Magnetic Resonance (NMR) Geophysical Measurements, J. of Applied Geophysics 34, pp. 277-282 (1994); SLICHTER, CHARLES P., Principles of Magnetic Resonance, 2nd Edition Springer Series in Solid-State Sciences, (1996); LEGCHENKO, et al., Nuclear Magnetic Resonance as a Geophysical Tool for Hydrogeologists, J. of Applied Geophysics 50, pp. 21-46 (2002); WEICHMAN, et al., Study of Surface Nuclear Magnetic Resonance Inverse Problems, J. of Applied Geophysics 50, pp. MOHNKE, et al., Smooth and Block Inversion of Surface NMR Amplitudes and Decay Times Using Simulated Annealing, J. of Applied Geophysics 50, pp. 163-177 (2002); SHUSHAKOV, et al., Hydrocarbon Contamination of Aquifers by SNMR Detection, WM'04 Conference, Feb. 29-Mar. 4, 2004, Tucson, Ariz.

SUMMARY OF INVENTION

In one embodiment of the present invention a method for detecting a liquid under a surface is provided. The method comprises locating a volume of substances under the surface, wherein at least a portion of the volume of substances is within a static magnetic field; transmitting at least one radio-frequency excitation pulse from a remote location above the volume of substances to generate a nuclear magnetic resonance (NMR) signal from the volume of substances; detecting, from the remote location, the NMR signal from the volume of substances; and processing the detected NMR signal to determine whether the volume of substances includes the liquid. In some exemplary embodiments the surface may be snow, ice, or water and the liquid may be hydrocarbons including crude oil.

In another embodiment of the present invention a method for mapping the presence of a liquid under a surface is provided. The method includes selecting an area of interest having a surface at least partially obscuring visual detection of substances below the surface; traversing the area of interest while using a detection method to gather data regarding the presence of the liquid under the surface, wherein a nuclear magnetic resonance (NMR) tool is used to conduct at least a portion of the detection method; and mapping the presence of the liquid under the surface using the gathered data. The detection method may be the method of the first embodiment of the present invention.

In a third embodiment of the present invention an apparatus for detecting a liquid hydrocarbon under a surface is provided. The apparatus comprises a nuclear magnetic resonance (NMR) tool having an antenna for sending and receiving signals mounted to an airborne platform and configured to receive the NMR tool and the antenna, wherein the antenna is a wire loop having a largest dimension of from about five meters to less than about twenty meters. The apparatus may be used in combination with the methods of the present invention.

In a fourth embodiment of the present invention, a method of characterizing ice is provided. The method includes locating, from a remote location, an air/surface interface within a volume of interest in a static magnetic field, wherein the surface is an upper ice surface; locating a liquid/surface interface within the volume of interest, wherein the surface is a lower ice surface; and determining the thickness of a body of ice in the volume of interest by calculating a distance between the air/surface interface and the liquid/surface interface. The step of locating the liquid/surface interface includes transmitting at least one radio-frequency excitation pulse from the remote location above the volume of interest to generate a nuclear magnetic resonance (NMR) signal from the volume of interest; detecting, from the remote location, the NMR signal from the volume of interest; and processing the detected NMR signal to determine the location of the liquid/surface interface within the volume of interest.

BRIEF DESCRIPTION OF THE DRAWINGS

The foregoing and other advantages of the present technique may become apparent upon reading the following detailed description and upon reference to the drawings in which.

DETAILED DESCRIPTION

In the following detailed description section, the specific embodiments of the present invention are described in connection with preferred embodiments. However, to the extent that the following description is specific to a particular embodiment or a particular use of the present invention, this is intended to be for exemplary purposes only and simply provides a description of the exemplary embodiments. Accordingly, the invention is not limited to the specific embodiments described below, but rather, it includes all alternatives, modifications, and equivalents falling within the true spirit and scope of the appended claims.

The term "surface" as used herein refers to a layer of aqueous material that obscures visual detection of substances below the surface. More specifically, the surface may be snow, ice, or a layer of water or any combination thereof, such as, for example, broken up ice floating in water. The term surface does not include non-aqueous surfaces such as earth or rock.

The present invention discloses a method of detecting a liquid under a surface. The method includes locating a volume of substances under the surface and located at least partially in a static magnetic field such as earth's magnetic field or a field generated by man-made equipment. The surface may be snow, ice, or water. Next, the method includes transmitting a signal from a remote location above the volume of substances to generate a nuclear magnetic resonance (NMR) signal from the volume of substances, detecting the NMR signal, and then processing the detected NMR signal to determine whether the volume includes the liquid, which may be hydrocarbons, specifically, an oil spill.

In at least one embodiment, the method includes transmitting a radio-frequency (RF) excitation pulse from the remote location to generate a nuclear magnetic resonance (NMR) signal from the volume of substances to be detected. The tool used to send and receive the signal may have a significantly smaller antenna or wire loop than existing NMR tools. For example, the loop may have a size of about ten meters or less or about 20 meters or less rather than a loop size of about 100 meters. The smaller loop size will decrease the effective volume and depth that can be detected, but also make the loop more manageable when mounted on an airborne platform. In the process of the present invention, one might adjust the shape and size of the loop depending on a variety of factors, including desired volume and depth to be detected. Many outside factors may affect the type of loop used, such as weather, ice conditions, size of the spill, and other factors.

In another embodiment of the present invention, a method of mapping a liquid under a surface is provided. The surface may be water, snow, or ice and the ice may be any of marine or freshwater ice, land-fast ice, moving ice, first year ice, multiyear ice, or pack ice; and the liquid may be a hydrocarbon crude oil, vegetable oil, mineral oil, or fuel oil. The method includes selecting an area of interest, which area may include a liquid under a surface that at least partially obscures visual detection of the liquid. Next, the area of interest is traversed while using a detection method to gather data about the presence of the liquid under the surface. A nuclear magnetic resonance (NMR) tool is used in at least a portion of the detection method. Further, the method includes mapping the presence of the liquid utilizing the data from the detection method.

Yet another embodiment of the present invention is an apparatus for detecting oil spilled under a surface such as water, snow, or ice. The apparatus may include a nuclear magnetic resonance (NMR) tool having an antenna for sending and receiving signals mounted to an airborne platform configured to receive the NMR tool, wherein the antenna is a wire loop having a diameter of less than about ten meters or less than about twenty meters.

Beneficially, the invention provides a method and system for remotely detecting a liquid under a surface using an airborne platform. The NMR signal produced directly from the oil can be generated from oil on the surface and down to ten, twenty, or more meters below the surface. The signal is not affected by the thickness of the surface nor conditions on the surface of the ice, including ice and snow cover. In fact, the structural characteristics of ice (and snow) make it effectively transparent to the NMR signal. Hence, the signal is unaffected by snow and ice cover, is less susceptible to false positives, the tool is compact enough to mount in an aircraft to eliminate the need to contact the surface, and capable of rapid detection.

Alternatively, methods are disclosed for characterizing ice in an arctic environment. One exemplary method may include locating an air/surface interface at the top of the ice and a liquid/surface interface at the bottom of the ice, then determining the thickness and other characteristics of the ice. The top surface may be detected by use of a laser to determine a height above the ice surface and the bottom surface may be detected using nuclear magnetic resonance technology.

Figure 1:
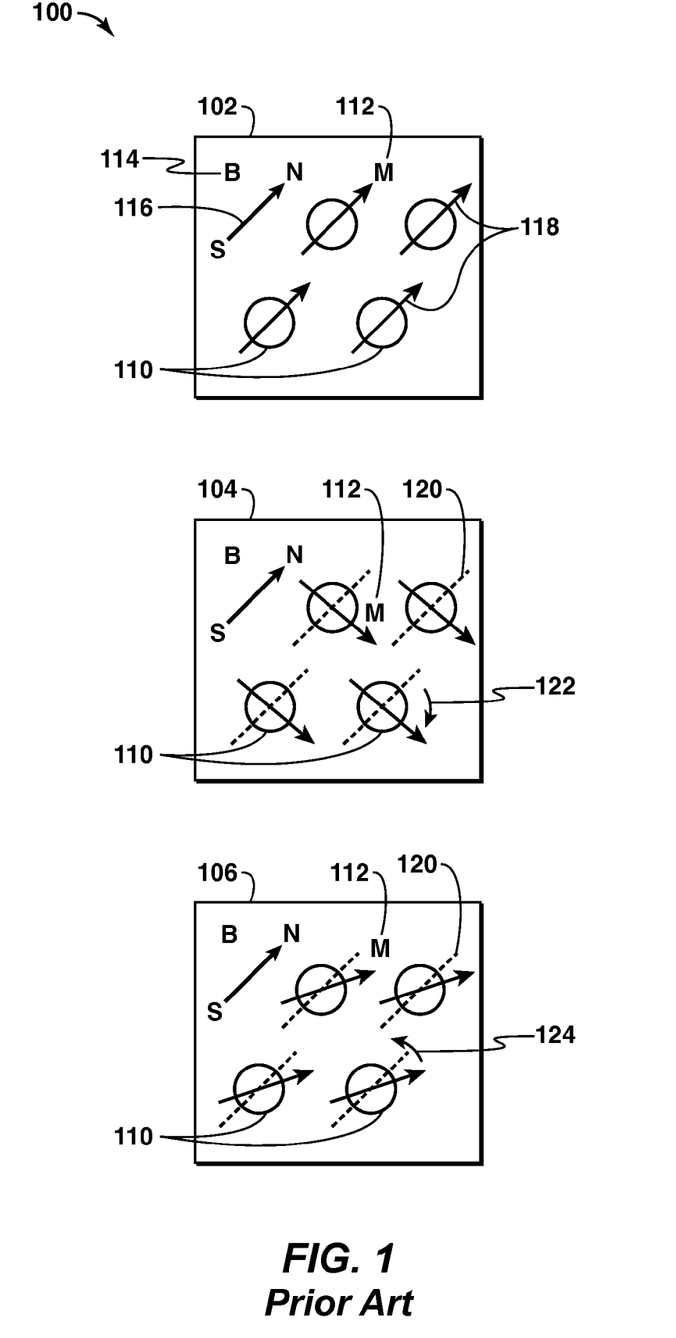
FIG. 1 illustrates an exemplary, simplified, two-dimensional display of the steps of a classical nuclear magnetic resonance detection process.

Referring now to the figures, FIG. 1 illustrates an exemplary, simplified, two-dimensional display of the steps of a classical nuclear magnetic resonance detection process 100. The process 100 includes an initial or equilibrium state 102, wherein a plurality of nuclei 110 each have a magnetic moment 112 having a heading 118 and a static magnetic field with a magnitude 114 and an orientation 116. In the initial state, the heading 118 of the magnetic moment 112 is aligned with the orientation 116 of the static magnetic field. The second state may be termed the disturbed state 104. In the disturbed state 104, a radio-frequency (RF) excitation pulse (e.g., apply an external electromagnetic field) is applied to the nuclei 110, the magnetic moments 112 rotate, move, or precess 122 from their equilibrium orientation 120. The third state may be termed the response or measurement state 106. In the response state 106, the RF excitation pulse is terminated and the magnetic moments 112 begin to rotate, move, or precess 124 back towards their equilibrium orientation 120. The movement back to equilibrium results in a loss of energy that produces a radio-frequency (RF) signal that may be measured. Certain characteristics of the RF signal are a function of the physical environment of the specific nuclei. Analysis of the RF signal allows differentiation between nuclei in a hydrocarbon molecule (e.g., crude oil) and nuclei in water.

For all NMR methods, the combination of the magnetic field and frequency of the excitation pulse are carefully selected to satisfy the relation $\omega = \gamma B$ where $\omega$ is the frequency, known as the Larmor frequency, B is the strength of the magnetic field 114 and $\gamma$ is the gyro-magnetic ratio of the proton or nuclei. The gyro-magnetic ratio $\gamma$ has a specific value for each type of nucleus 110, and hence the Larmor frequency is a physical property of the nuclei 110. By selecting the Larmor frequency, one can decide which nuclei will be detected or investigated. The intensity or magnitude of induced transverse magnetization, Mx,y(t), is monitored as the protons 110 in the molecules of the liquid return to thermal equilibrium 106. This time dependence generally follows an exponential decay:

$$M_{x,y}(t) = M_0 \exp(-t/T_{2B}) \quad (1)$$

In Equation 1, the initial amplitude, $M_0$, at t=0 is proportional to the concentration of liquid molecules within the detected volume and $T_{2B}$ is the transverse relaxation time (or response time) of the liquid of interest. The amplitude Mx,y(t) is detected as a time varying voltage in a radio-frequency receiver antenna. When multiple types of molecular environments (e.g. fluids) are present, it is possible that each fluid will have its own characteristic relaxation time, $T_{2Bi}$, which is associated with a magnetization, $M_{0i}$. In this case, the total transverse magnetization detected for the bulk fluid will be:

$$M_{x,y}(t) = \sum_i M_{0i} \exp(-t/T_{2Bi}) \quad (2)$$

Equation 2 also describes the time evolution of the transverse magnetization for complex fluids such as petroleum. Petroleum is comprised of a very large number of hydrocarbon molecules 110, which are each described by a characteristic NMR relaxation time, $T_{2Bi}$. In such complex molecules 110, the relaxation time may differ slightly for each molecule found in the fluid. However, the relaxation times for hydrogen nuclei in petroleum are sufficiently similar to each other and sufficiently different from the hydrogen nuclei in water that the two fluids can be generally differentiated using this type of relaxation analysis.

In the analytical applications of NMR, where measurements are made in strong, homogeneous magnetic fields, the NMR signal of protons in water are distinguished from those of protons in other liquids, such as hydrocarbons, by observing small frequency differences in the resonance frequencies. These frequencies are too small to detect when operating in the low RF frequencies (e.g. about 2 kilo Hertz (kHz)) required to measure the proton NMR signal in the earth's magnetic field. However, as mentioned, the protons in hydrocarbon oils have NMR relaxation properties that are sufficiently different from those of the protons in water that the relaxation differences can serve to differentiate signals from water and oil at the low frequency required to measure the NMR signal in the earth's magnetic field.

The NMR signal may be processed to obtain the "spectrum" of T2 values for the fluids as a function of depth. However, it is generally sufficient just to know whether oil is present below the ice and the volume of oil if it is present for the present application. For this purpose, it may not be necessary to invert the detected signal to resolve the depth dependent signal response, since the water and oil signals are identified by their characteristic values of T2.

One potential complicating factor is enhancement of the NMR relaxation rate for liquid located near a solid surface (such as a body of ice) or in a crack or pore of the solid body. Fluid molecules that interact with a surface experience an enhancement of the NMR relaxation rate. The surface relaxation rate, 1/T2S, is determined by the product of the intrinsic surface relaxivity rate, $\rho$, and the surface-to-volume ratio, S/V. The surface relaxivity, $\rho$, is related to the wettability of the surface by the fluid. Strongly wetting fluids will have a larger $\rho$ while non-wetting fluids will have a smaller $\rho$.

For water and light oils, the more typical issue is that the diffusion of the fluid results in an exchange (or mixing) of the fluid at the surface with the fluid in the bulk. In this case, a single exponential is observed for the transverse magnetization decay for all pores which have a similar surface relaxivity and pore radius. The macroscopic magnetization is then determined by the summation of the NMR signals over all pores and fluid types:

$$M_{x,y}(t) = \sum_{i,j} M_{oi,j} \exp(-t/T_{2i,j}) \quad (3)$$

As mentioned, a variety of different NMR signals, including but not limited to T2*, T2, T1 can be measured and used to differentiate between the water and oil signals. The relaxation time T2* describes the time constant for the loss of phase coherence of the transverse magnetization after the RF excitation field is turned off. This time dependent loss of phase coherence may be referred to as the free induction decay. The time constant T2 describes the characteristic decay time for the loss of phase coherence of the transverse magnetization following an application of two (or more) RF pulses. If two RF pulses are applied which are separated in time by $\tau$, an NMR nuclear spin echo is formed at time $2\tau$, The time dependence of the amplitude of the echo is described by Equation 3 with t=$2\tau$. In this mode of measurement, the pair of RF pulses is repeated by successively increasing the delay time $\tau$, between the first and second RF pulse. In an alternative embodiment of this method, known as the CPMG (Can Purcell Meiboom Gill) pulse sequence, a long series of RF "refocusing" pulses are applied every $2\tau$, time intervals following the first pulse. This generates a spin echo following every time period $\tau$, following the second pulse.

For the purpose of the present invention, the primary advantage for collecting the NMR spin echo data in this multiple pulse excitation mode is to increase the speed of data collection, which can translate to a higher signal to noise ratio. Another option is to measure the proton T1 value, which is the characteristic time for the longitudinal magnetization to return to thermal equilibrium. There are different experimental approaches for measuring the T1 value. One common method is the so-called inversion recovery method in which a sufficiently strong RF pulse is appropriately applied to either squelch or actually invert the magnetization. The return to thermal equilibrium is then monitored by sampling the state of the magnetization over time either by a series of free induction measurements or spin echo measurements.

Generally, the nuclei 110 of unique substances will generate unique responses (e.g. relaxation times). Hence, one excitation pulse may permit measurement of multiple substances in a particular volume. For example, water displays a different response than oil, allowing differentiation between the two depending on the proton or nuclei's response to the excitation pulse. Also, substances having different physical states will respond differently. For example, ice responds to an excitation pulse differently from water because of the structured nature of ice crystals. More particularly, the magnetic moment 112 of hydrogen nuclei in ice and snow returns to its equilibrium state 102 so quickly that it becomes undetectable or "invisible" to standard NMR equipment.

In applications to geophysical prospecting for ground water detection in sub-surface aquifers, a single conductor loop has been used for both generating the oscillating magnetic field in the sub-surface as well as for detecting the NMR signal generated in the sub-surface. However, more complex antenna configurations have also been used, including the use of a separate receiver antenna and more complex transmitter/receiver loops such as a figure eight. These alternative antenna arrangements may used to increase the sensitivity of detection. More complex antenna configurations are also used to localize the source of the NMR signal in the sub-surface. Such antenna configurations are compatible with and contemplated by the present invention and may be used in combination therewith in accordance with the knowledge of a person skilled in the art.

The maximum depth of investigation is approximately proportional to the size of the antenna. For example, for a single conductor loop with diameter D, the maximum depth of investigation is of order D. In the geophysical exploration for ground water in the sub-surface, the depths of investigation of interest are on the order of 100 meters (m) which require an antenna loop approximately 100 m in diameter.

Figure 2A:
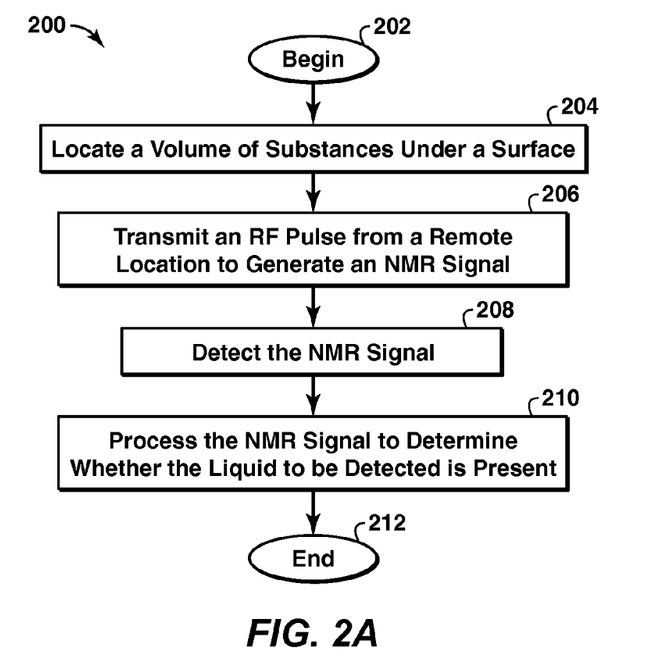
FIG. 2A shows a flow chart of one embodiment of a method of detecting a liquid under a surface.

FIG. 2A shows a flow chart of one embodiment of a method of detecting a liquid under a surface using some of the terminology of FIG. 1 and in accordance with certain aspects of the present invention. Hence, FIG. 2A may be best understood with reference to FIG. 1. The method 200 begins at 202, then a volume of substances under the surface are located 204. At least a portion of the volume of substances is in a static magnetic field, which may be the earth's magnetic field or a magnetic field generated by a man-made instrument. A radio-frequency (RF) excitation pulse is then transmitted from a remote location 206. The RF excitation pulse may be in the form of a radio-frequency excitation pulse, an electromagnetic pulse, or other pulse configured to generate a nuclear magnetic resonance (NMR) response signal from the volume of substances. Then the NMR signal is detected 208 and the detected NMR signal is processed 210 to determine whether the volume of substances includes the liquid to be detected.

The detecting 208 is preferably done from the remote location and may be done using at least part of the same tool that generated the excitation pulse 206. However, it should be noted that the term "detecting" may include simply recording by an automated process and does not specifically require human monitoring or display of data or results on a monitor as part of the function of the tool. In fact, the "detecting" may simply be recording data for later review at another location.

The step of processing 210 may be made at the remote location on a real-time or close to real-time basis, as in within one minute of the detecting step 208. Alternatively, the processing 210 may be done well after steps 202-208 have been completed and possibly repeated, with data resulting from those steps recorded for a variety of discreet locations. The step of processing 210 includes reviewing the relaxation times of the substances located in the volume to be detected and comparing those relaxation times to relaxation times of known substances, such as water and hydrocarbons. Then, the process may end at block 212. Hydrocarbon liquids may include any type of crude oil or a processed oil, such as vegetable oil, mineral oil, or fuel oil.

In one alternative embodiment, the remote location is an airborne platform located above the volume to be detected. The airborne platform may be a rotary wing aircraft, vertical take-off and landing aircraft (VTOL), a lighter-than-air craft, or other craft that can move over a volume to be detected or hold a position over the volume.

In one embodiment, the steps of sending a pulse 206 and detecting NMR signals 208 may be carried out using a standard, modified, or custom-built nuclear magnetic resonance (NMR) tool. The relaxation times may include a free induction signal (T2*), a spin echo signal (T2), a train of spin echo signals (T2), and a thermal equilibrium signal (T1), as described above. In some embodiments, the NMR tool may also provide the static magnetic field 204, but preferably, the static magnetic field is the Earth's magnetic field. The NMR tool may be a modified off-the-shelf tool, such as the NUMIS™ from Heritage Geophysics or may be a fully customized tool or some combination of off-the-shelf and customized components.

In one alternative embodiment, the wire loop for the NMR tool may be modified to carry out the steps of the present invention. A standard NMR tool such as the NUMIS™ includes a 100 meter (m) loop. However, such an antenna may be too large and unwieldy for the steps of the present method, so a smaller loop is preferred. The loop size and configuration may be determined by the airborne platform, the timing, depth of detection desired, response time, and weather conditions. The antenna loop may have a "FIG. 8" configuration, a single loop, multiple loops, or some combination thereof. One may prefer to use a copper tube as the antenna loop as it may be sturdier. As noted, the depth desired is approximately proportional to the diameter of the loop. Hence, a loop of 10 meters provides a depth of 10 meters and a loop of 20 meters provides a depth of 20 meters. In one exemplary embodiment, the loop is from about 10 to about 20 meters in diameter depending on the conditions.

The remote location may be only a few inches above the surface over the volume of substances to be determined. This will depend primarily (though not solely) on the depth and total volume that may be detected using steps 204-208. The depth and total volume that may be detected will depend largely on the type of equipment used, but the depth should be at least about five meters, preferably about ten meters, and more preferably about 20 meters. A depth of about 5 meters would require the remote location to be no more than one meter or so above the ice as some ice can be as thick as 1-3 meters and the depth of detection must extend below the ice. Similarly, a depth of ten meters would permit the remote location to be about five meters above the surface and larger depths would allow greater height above the surface of the ice.

One alternative embodiment of the method contemplates moving to another volume of substances to be detected and repeating at least steps 206 and 208 for that volume. These additional volumes may be detected in a continuous fashion or iteratively. If done continuously, there may be some "smearing" of signals, which may be addressed by those of skill in the art using well known techniques. Such a process could be repeated for many volumes of detection. Step 210 may be conducted after the other steps have been repeated several times for several different volumes of substances. These volumes of substances would likely lie in a field of ice in an ice-prone environment at an area of interest where an oil spill is suspected. After taking repeated measurements, the location or area of interest may be mapped to determine a location, shape, and size of an oil spill if there is an oil spill under the ice. Once an initial map is made, the steps 204-210 may be repeated at different locations or for longer time periods to refine the map and continuous monitoring may be conducted to determine any changes over time in the character of the oil spill.

The detection method 200 may be applied in a large variety of locations (e.g. areas of interest) and applications. Examples includes detecting oil spilled under ice in an arctic or sub-arctic region as part of remediation, clean-up or other oil spill response effort; detecting natural seeps of oil and other hydrocarbons in ice and snow-covered regions as part of oil exploration efforts; and monitoring or detecting spills or leaks from man-made structures such as storage tanks and pipelines that may be fully or partially covered by ice and/or snow. In each of the exemplary cases, the liquids to be detected are at least partially shielded from visual detection by some combination of ice and snow and remote detection is preferred, although a land or sea vehicle having a boom arm or similar device for supporting the detection equipment may be preferable to a helicopter.

Figure 2B:
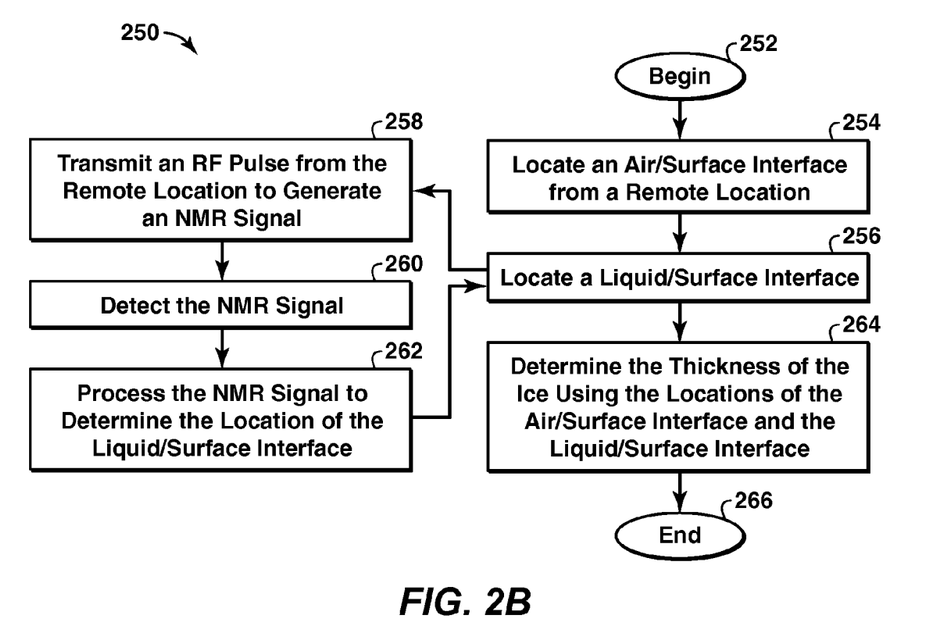
FIG. 2B shows a flow chart of one embodiment of a method of characterizing ice from a remote location.

FIG. 2B shows a flow chart of one embodiment of a method of characterizing ice from a remote location using some of the concepts from FIGS. 1 and 2A. As such, FIG. 2B may be best understood with reference to FIG. 1. FIG. 2B shows a method 250 beginning at box 252 and including locating an air/surface interface at the top of a volume of ice 254 from a remote location, locating a liquid/surface interface at the bottom of the volume of ice 256, and determining the thickness of the ice 264 using the locations of the air/surface interface and the liquid/surface interface. The step of locating the liquid/surface interface 254 includes transmitting at least one radio-frequency excitation pulse from the remote location above the volume of ice to generate a nuclear magnetic resonance (NMR) signal from the volume of ice 258; detecting, from the remote location, the NMR signal from the volume of ice 260; and processing the detected NMR signal 262 to determine the location of the liquid/surface interface within the volume of interest.

The method 250 may include an analysis of the nature of the ice, such as marine or freshwater ice, land-fast ice, moving ice, first year ice, multiyear ice, or pack ice. This information may be determinable by examining the NMR signal or by another method, such as by optical observation, an interpretation based on the thickness, another technique know to those of skill in the art, or an equivalent technique. The air/surface interface may be located 254 using a number of techniques and apparatuses, including a range-finding laser, an altimeter, radar, an elongated member, or some combination of these or equivalent devices. The device generally functions to locate the upper surface of the ice, which may be visible to the naked eye or may be completely covered by snow, fog, or other visual obstruction.

Figure 3:
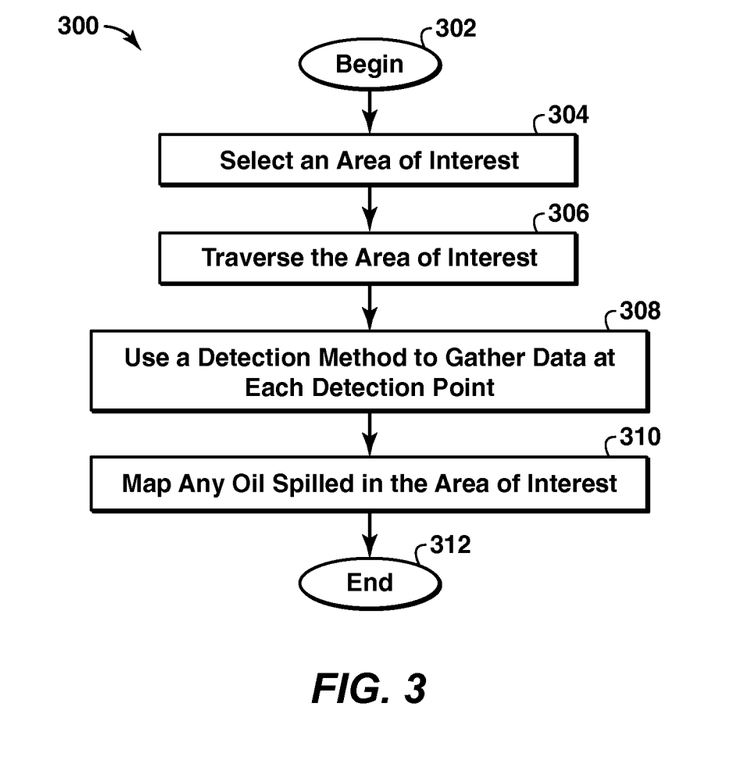
FIG. 3 shows a flow chart of another embodiment of a method of mapping the presence of a liquid under a surface.

FIG. 3 shows a flow chart of another embodiment of a method of mapping the presence of a liquid under a surface. Some of the steps of FIGS. 2A-2B may be referenced in connection with FIG. 3. As such, FIG. 3 may be best understood with reference to FIGS. 2A-2B. The method 300 begins at block 302. Then, an area of interest is selected 304. The area of interest preferably including a surface at least partially obscuring visual detection of substances below the surface, wherein the area of interest is suspected of having the liquid under the surface. Note that the area of interest may be at least any of the exemplary areas of interest mentioned above in connection with the detection methods 200 or 250. Such areas include an offshore area having a suspected oil spill, an onshore or offshore location that may have a hydrocarbon seep, and an onshore location that may have oil leaking from a pipeline, tank, or other manmade structure. Once the area of interest is selected, the area of interest is traversed 306 while using a detection method to gather data regarding the presence of the liquid under the surface. A nuclear magnetic resonance (NMR) tool is used to conduct the detection method, which may be the methods discussed in relation to FIGS. 2A-2B above.

The traversing step 306 may be conducted by the airborne platform as disclosed above. Traversing may include stopping at each of the predefined detection points to use a detection method to gather data 308 if the method is to be conducted iteratively. However, it may be preferable to continuously traverse the area of interest without stopping in order to obtain results more quickly. In some embodiments, there may be occasion to bypass a particular detection point or add a detection point as the data is gathered. Such an adjustment may be dictated or affected by weather conditions or new data gathered at a detection point or group of detection points. Next, mapping of the oil spilled in the area of interest 310 may be conducted using the data gathered in step 308. The mapping 310 may be as simple as hand drawing the oil spill based on readings from the detection method, but may include detailed, three-dimensional maps of oil under the ice if the gathered data is sufficient enough and in the proper format. Then the process may end at block 312.

Optionally, there may be a planning step before the traversing step 306. The planning step may include a singular or collaborative mental exercise based on experience, or may include consideration of mapping, global positioning system (GPS), weather, ice conditions, or other data, or may include predictions of the oil location from a numerical model and may even include a computer program designed to efficiently plan a route for the given data inputs.

In order to effectively take readings at multiple locations in an area of interest, it may be important to take measurements more quickly than a standard nuclear magnetic resonance tool or technique. In at least one alternative embodiment, the substance(s) to be detected include relatively large volumes such as macroscopic pods, pools, or clumps of hydrocarbon oil trapped within or under the ice. Note that the oil may be emulsified oil or weathered oil, which may be neutrally buoyant. In such a case, the oil may be several meters below the surface with a layer of liquid water between the surface and the oil. For an environment containing oil, ice, and water, step 208 of FIG. 2 should detect NMR signals from the nuclei or protons in the oil and the water. As pointed out, the NMR relaxation of protons for the water frozen in the ice is too rapid for detection making the ice effectively invisible to NMR. In one embodiment of the present techniques, the data processed in step 210 is no more than a "yes" or "no" reading. In other words, there is no need to closely analyze the signal in this embodiment to determine interaction between the oil, water, and ice or pore size and other characteristics. As such, less complete data is needed in this embodiment, permitting a more rapid traverse 306. In this embodiment, the monitoring time may take from about 5 seconds to about ten seconds. In the iterative case, the monitoring time may extend from about 30 seconds to about one minute, or from about one minute to about five minutes, or from about five minutes to about ten minutes for each volume of substances to be detected.

In one embodiment of the present invention, the method of steps 302-312, particularly the data gathering step 308, may include the detection method of steps 202-212 above or steps 254-264. The method may also include other embodiments of those steps as discussed in greater detail in connection with the discussion of the methods 200 or 250. For example, the detection method may include an NMR tool for sending the excitation pulse and receiving the signal from the nuclei, the wire loop may be copper tubing, wire, or other construction, and the airborne platform may operate at a height of about 10 meters or less over the volume to be detected, or about 20 meters or less over the volume to be detected.

Figure 4A:
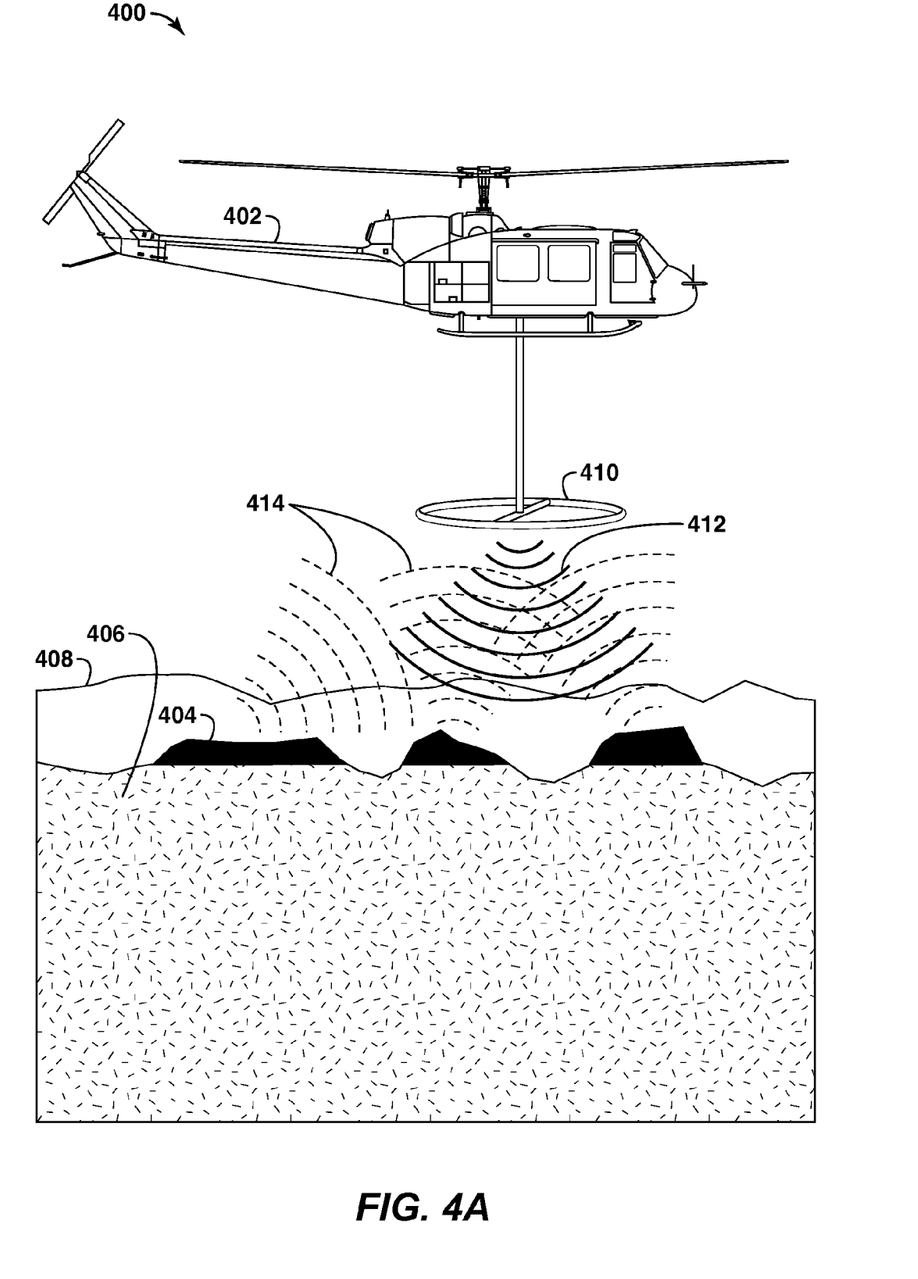
FIG. 4A is an exemplary illustration of a helicopter remotely positioned over a location and having a nuclear magnetic resonance (NMR) device operatively attached thereto for detecting a liquid under a surface in accordance with certain aspects of the methods of FIGS. 2A and 3.

FIG. 4A is an illustration of a helicopter hovering over a location and having a nuclear magnetic resonance device operatively attached thereto for detecting a liquid under a surface in accordance with certain aspects of the method of FIGS. 2A and 3. As such, FIG. 4A may be best understood with reference to FIGS. 2A and 3. The helicopter 402 is at a location 400 for detecting oil under ice in accordance with the methods of FIG. 2A or 3. The helicopter is equipped with a nuclear magnetic resonance (NMR) tool having a NMR antenna 410; and other components that may be located within the helicopter 402. The NMR tool 410 is sending signals 412 and receiving signals 414 from the volume below the helicopter 402, which includes a body of water 406, a surface 408, and a liquid to be detected 404.

In one embodiment, the helicopter 402 may be substituted for another airborne platform, or a surface vessel having a boom, the NMR tool 410 may or may not hang below the helicopter 402, but may be attached to the underside or skids or some other combination. The body of water 406 may be marine or fresh (e.g. lacustrine), the surface 408 may be water, snow, or ice and the ice is marine or freshwater ice, land-fast ice, moving ice, first year ice, multiyear ice, pack ice or some combination thereof. The liquid to be detected 404 may be a hydrocarbon crude oil, vegetable oil, mineral oil, and fuel oil. There may not be oil between the ice and the water, the oil 404 may be slightly below the surface of the water 406 or may be at least partially trapped inside the ice 408 or at least partially mixed with the water 406.

Preferably, the NMR remote-detection apparatus device 410 includes an electric current generator capable of producing an alternating current of the desired Larmor frequency (roughly 1-3 kHz for hydrogen in the Earth's magnetic field); a transmitter/receiver unit for generating low frequency excitation pulses and measuring the resulting signal; a transmitter/receiver antenna; and a computer for controlling the system, storing the data, and performing interpretations.

Alternatively, the NMR remote-detection apparatus device 410 may further include a magnetic field generator or permanent magnet capable of developing a strong, homogenous magnetic field in the volume of substances to be detected.

Figure 4B:
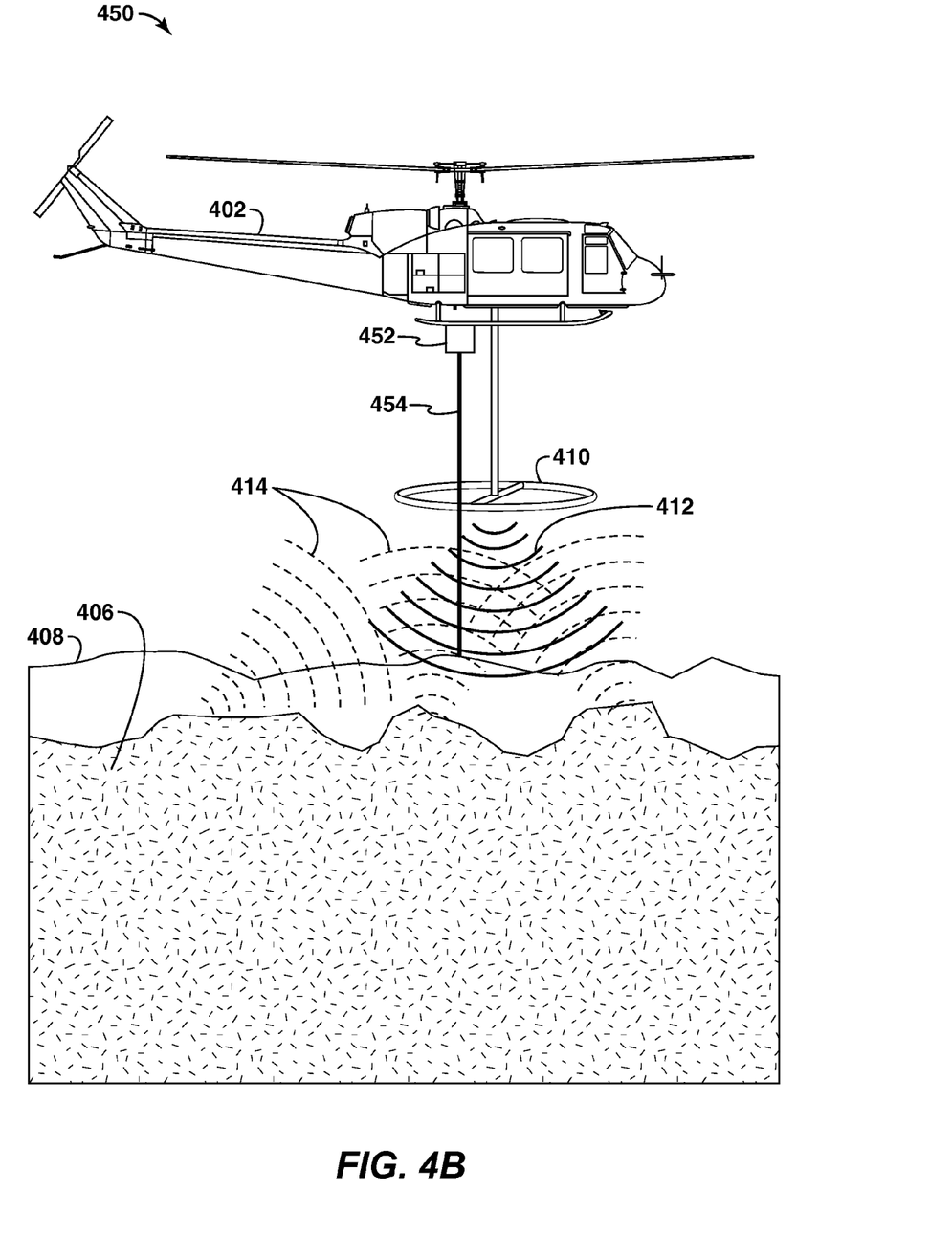
FIG. 4B is an exemplary illustration of a helicopter remotely positioned over a location and having an NMR device and another remote sensing device attached thereto for detecting an upper surface and lower surface of ice in accordance with certain aspects of FIG. 2B.

FIG. 4B is an exemplary illustration of a helicopter remotely positioned over a location and having an NMR device and another remote sensing device attached thereto for detecting an upper surface and lower surface of ice in accordance with certain aspects of the methods of FIG. 2B. As such, FIG. 4B may be best understood with reference to FIG. 2B. Further, to the extent that reference numbers are the same between FIGS. 4A and 4B, the referenced items may be considered equivalent. The exemplary apparatus 450 includes many of the same features as apparatus 400, but further includes a detection device 452 and a detection signal 454 emanating from the device 452. In one example, the device 452 may be a laser generator and the signal 454 may be the emitted laser for determining the location of the air/surface interface 254. Alternatively, the device 452 and signal 454 may be the same, such as when using an elongated member.

EXPERIMENTAL RESULTS

Figure 5A:
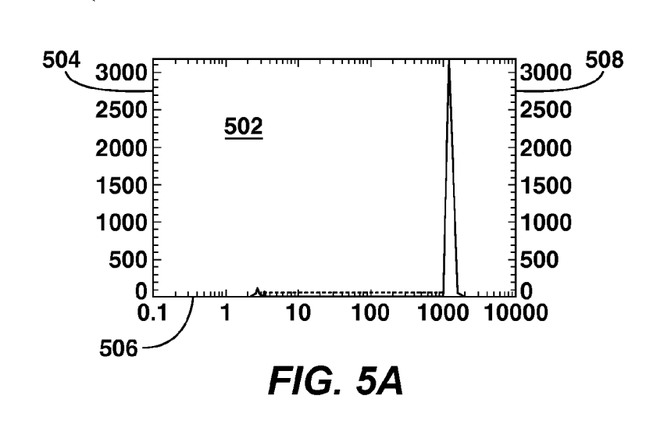
FIGS. 5A-5C show the amplitude peaks from nuclear magnetic resonance (NMR) tests to determine the T2 spectrum for mixtures of oil, seawater, and ice.
Figure 5B:
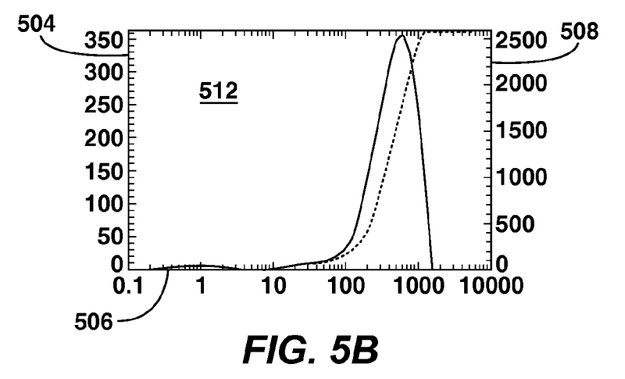
Figure 5C:
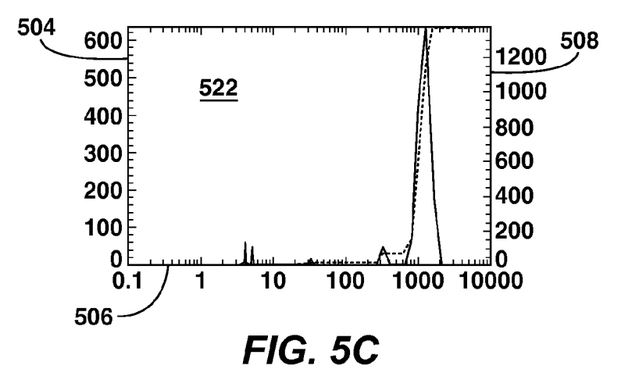

FIGS. 5A-5C show graphs 500 of amplitude peaks from nuclear magnetic resonance (NMR) tests to determine the T2 spectrum for mixtures of oil, seawater, and ice. A laboratory demonstration was conducted to show that the water and oil signals from water and oil trapped under ice can be differentiated from the differences in their relaxation properties. These tests indicate that the NMR method can detect a direct signal from oil in ice. FIG. 5A shows the NMR T2 signal for seawater alone 502 maintained at near 0 degrees Celsius (° C.). Each graph 502, 512, and 522 include measures of the incremental signal measurement 504 on the left vertical axis and shown as a solid line, the cumulative signal measurement 508 on the right vertical axis and shown as a dashed line, and the spin echo relaxation time T2 506 (in milliseconds (ms)) on the horizontal axis. Note that the seawater graph 502 shows a T2 peak at about 1200 milliseconds (ms), which is the known T2 for bulk water. FIG. 5B shows the T2 signal for the bulk crude oil 512 at 0° C. It has a peak at about 500-600 ms, clearly distinguishable from the seawater signal 502. FIG. 5C shows the amplitude peaks from a 20 milliliter (ml) sample of sea ice into which 0.3 ml of oil has been injected 522. The large signal from the melted seawater is observed at 1100 ms as expected. We also observe a small signal at 300 ms which is assigned to the oil. The shift to smaller T2 values from that of the bulk oil is expected because of surface interaction with the ice. Significantly, the experimental results show that the water and oil peaks are clearly differentiable.

Beneficially, the NMR remote detection techniques disclosed herein provide a solution to a need for oil spill response in ice prone environments that has existed for over 30 years. It has the benefits of providing a direct signal from the oil itself that is not attenuated by the ice. In addition, the airborne capability allows rapid inspection of large areas without placing personnel and equipment directly on top of ice.

While the present invention may be susceptible to various modifications and alternative forms, the exemplary embodiments discussed above have been shown only by way of example. However, it should again be understood that the invention is not intended to be limited to the particular embodiments disclosed herein. Indeed, the present invention includes all alternatives, modifications, and equivalents falling within the true spirit and scope of the appended claims.

What is claimed is:

1. A method for detecting a liquid under a surface, comprising:
    a) locating a volume of substances under the surface, wherein at least a portion of the volume of substances is within a static magnetic field;
    b) transmitting at least one radio-frequency excitation pulse from a remote location above the volume of substances to generate a nuclear magnetic resonance (NMR) signal from the volume of substances;
    c) detecting, from the remote location, the NMR signal from the volume of substances;
    d) processing the detected NMR signal to determine whether the volume of substances includes the liquid, and
    e) moving the remote location to another area of interest in an ice-prone region and repeating steps b) through d) for the another volume of substances, wherein
    processing the detected nuclear magnetic resonance (NMR) signal comprises interpreting data selected from the group consisting of the intensity of the NMR signal, the relaxation time of the NMR signal, and any combination thereof, and
    the area of interest is selected from the group consisting of an offshore arctic or sub-arctic area for detection of an oil spill for the purpose of oil spill remediation, an offshore or onshore arctic or sub-arctic area for detection of an oil seep for the purpose of hydrocarbon exploration, and an onshore arctic or sub-arctic area for detection of oil leaks from man-made structures for the purposes of remediation and repair of the structures.

2. The method of claim 1, wherein the surface is snow or ice and the ice is selected from the group consisting of marine ice, freshwater ice, land-fast ice, moving ice, first year ice, multiyear ice, pack ice, and any combination thereof.

3. The method of claim 1, wherein the liquid is selected from the group consisting of a hydrocarbon crude oil, mineral oil, fuel oil, and any combination thereof.

4. The method of claim 1, wherein the method is continuous throughout the area of interest and steps b) through d) are repeated until one of: i) the liquid is detected under the surface in the area of interest; ii) the liquid is mapped under the surface in the area of interest; or iii) it is determined that the liquid is not present under the surface in the area of interest.

5. The method of claim 1, wherein the relaxation time of the NMR signal is selected from the group consisting of a free induction signal (T2*), a spin echo signal (T2), a train of spin echo signals (T2), a thermal equilibrium signal (T1), and any combination thereof.

6. The method of claim 1, wherein the remote location is an airborne platform positioned substantially vertically above the volume of substances to be detected.

7. The method of claim 6, wherein the airborne platform is one of a helicopter and a lighter-than-air vehicle.

8. The method of claim 1, wherein the static magnetic field is one of the Earth's natural magnetic field and a magnetic field generated by a man-made device.

9. The method of claim 1, wherein the remote location is from less than one meter above the surface to about ten meters above the surface.

10. The method of claim 1, wherein the method is iterative throughout the area of interest and steps b) through d) are repeated until sufficient data is gathered to map the presence of the liquid in the area of interest.

11. The method of claim 1, wherein at least steps b) and c) are conducted using a nuclear magnetic resonance (NMR) tool, wherein the NMR tool comprises a conductive wire loop configured to at least transmit the at least one radio-frequency excitation pulse and to detect the at least one NMR signal from the volume of substances.

12. The method of claim 11, wherein the conductive wire loop has a largest dimension, wherein the largest dimension is from at least about five meters to about twenty meters.

13. A method of mapping the presence of a liquid under a surface, comprising:
    a. selecting an area of interest having a surface at least partially obscuring visual detection of substances below the surface;
    b. traversing the area of interest while using a detection method to gather data regarding the presence of the liquid under the surface, the detection method comprising:

i) locating a volume of substances under a surface in the area of interest, wherein at least a portion of the volume of substances is within a static magnetic field;

ii) transmitting at least one radio-frequency excitation pulse from a remote location above the volume of substances to generate a nuclear magnetic resonance (NMR) signal from the volume of substances;

iii) detecting, from the remote location, the NMR signal from the volume of substances; and iv) processing the detected NMR signal to determine whether the volume of substances includes the liquid, and c. mapping the presence of the liquid under the surface using the gathered data wherein the area of interest is selected from the group consisting of an offshore arctic or sub-arctic area for detection of an oil spill for the purpose of oil spill remediation, an offshore or onshore arctic or sub-arctic area for detection of an oil seep for the purpose of hydrocarbon exploration, and an onshore arctic or sub-arctic area for detection of oil leaks from man-made structures for the purposes of remediation and repair of the structures.

14. The method of claim 13, wherein the surface is water, snow, or ice and the ice is selected from the group consisting of marine ice, freshwater ice, land-fast ice, moving ice, first year ice, multiyear ice, pack ice and any combination thereof.

15. The method of claim 13, wherein the liquid is selected from the group consisting of a hydrocarbon crude oil, vegetable oil, mineral oil, fuel oil, and any combination thereof.

16. The method of claim 13, wherein processing the detected nuclear magnetic resonance (NMR) signal comprises interpreting at least one of the intensity of the NMR signal and the relaxation time of the NMR signal, wherein the relaxation time of the NMR signal is selected from the group consisting of a free induction signal (T2*), a spin echo signal (T2), a train of spin echo signals (T2), a thermal equilibrium signal (T1), and any combination thereof.

17. The method of claim 13, further comprising planning a route within the area of interest.

18. The method of claim 13, wherein the detection method is selected from the group consisting of: i) continuous throughout the area of interest ii) iterative throughout the area of interest, and any combination thereof.

* * * * *